(12) United States Patent
Kim et al.

(10) Patent No.: US 8,966,697 B2
(45) Date of Patent: Mar. 3, 2015

(54) ELECTRIC TOOTHBRUSH WITH EXCELLENT VIBRATION EFFICIENCY

(75) Inventors: Sung-Jin Kim, Daejeon (KR); Sug-Youn Chang, Seoul (KR); Jae-Hyun Ahn, Daejeon (KR); Kyung-Sub Lee, Chungcheongnam-do (KR)

(73) Assignee: LG Household & Health Care Ltd., Seoul (KR)

( * ) Notice: Subject to any disclaimer, the term of this patent is extended or adjusted under 35 U.S.C. 154(b) by 0 days.

(21) Appl. No.: 13/639,981

(22) PCT Filed: Apr. 7, 2011

(86) PCT No.: PCT/KR2011/002456
§ 371 (c)(1),
(2), (4) Date: Jan. 7, 2013

(87) PCT Pub. No.: WO2011/126326
PCT Pub. Date: Oct. 13, 2011

(65) Prior Publication Data
US 2013/0117949 A1    May 16, 2013

(30) Foreign Application Priority Data

Apr. 8, 2010  (KR) .......... 10-2010-0032356
Feb. 21, 2011 (KR) .......... 10-2011-0015057
Apr. 4, 2011  (KR) .......... 10-2011-0030706

(51) Int. Cl.
*A61C 17/22*  (2006.01)
*A61C 17/16*  (2006.01)
*A46D 3/04*   (2006.01)
*A61C 17/34*  (2006.01)

(52) U.S. Cl.
CPC ............... *A61C 17/16* (2013.01); *A46D 3/045* (2013.01); *A61C 17/3481* (2013.01)
USPC ........................................... 15/22.1

(58) Field of Classification Search
USPC ............................... 15/22.1, 23, 28
See application file for complete search history.

(56) References Cited

U.S. PATENT DOCUMENTS

| | | | | | |
|---|---|---|---|---|---|
| 2,489,582 | A  | * | 11/1949 | McCready | 15/22.1 |
| 6,802,097 | B2 | * | 10/2004 | Hafliger et al. | 15/22.1 |
| 7,805,794 | B2 | * | 10/2010 | Taggart et al. | 15/22.2 |
| 8,342,187 | B2 | * | 1/2013  | Kalman et al. | 132/119.1 |

FOREIGN PATENT DOCUMENTS

| | | |
|---|---|---|
| JP | 06-304021 A   | 11/1994 |
| JP | 3082502 U     | 9/2001 |
| JP | 2007-061209 A | 3/2007 |
| JP | 2008-080099 A | 4/2008 |
| JP | 2009-045202 A | 3/2009 |
| JP | 2009-106355 A | 5/2009 |
| JP | 2009-0279463  | 12/2009 |
| KR | 20-0323839    | 8/2003 |
| KR | 10-0999270    | 12/2010 |

* cited by examiner

*Primary Examiner* — Randall Chin
(74) *Attorney, Agent, or Firm* — McDermott Will & Emery LLP

(57) ABSTRACT

The present disclosure relates to an electric toothbrush, and more particularly, to an electric toothbrush, which has excellent vibration efficiency since vibrations of the vibration motor are directly transferred to the bristle holder, saves the battery power, reduces a size of the toothbrush, decreases the thickness of the head portion, allows the vibration motor to be stably fixed in a fixing groove formed at the upper surface of the head portion, and reduces noise.

10 Claims, 6 Drawing Sheets

ELECTRIC TOOTHBRUSH WITH EXCELLENT VIBRATION EFFICIENCY

RELATED APPLICATIONS

This application is the U.S. National Phase under 35 U.S.C. §371 of International Application No. PCT/KR2011/002456, filed on Apr. 7, 2011, which in turn claims the benefit of Korean Application No. 10-2010-0032356 filed on Apr. 8, 2010, Korean Application No. 10-2011-0015057filed on Feb. 21, 2011, and Korean Application No. 10-2011-0030706 field on Apr. 4, 2011, the disclosures of which Applications are incorporated by reference herein.

TECHNICAL FIELD

The present disclosure relates to an electric toothbrush, and more particularly, to an electric toothbrush showing excellent vibration efficiency since vibrations of a vibration motor are directly transferred to a bristle holder, allowing the vibration motor to be stably fixed to the upper surface of a head portion, and is capable of reducing noise.

BACKGROUND ART

Generally, an electric toothbrush is a tool that uses a vibration motor to vibrate a bristle holder holding the bristles to clean teeth. Usually, an electric toothbrush has a grip and a head portion, wherein a vibration motor and a battery are received in the grip, and the bristle holder is provided at the head portion.

The vibration motor installed at the grip is operated by the power of the battery to generate vibrations. The vibrations then transfer to the head portion to vibrate the bristle holder. In other words, the vibrations are not directly generated at the head portion but generated at the grip and then transferred to the head portion. During this vibration transferring procedure, the vibrations partially disappear or are transferred to the hand. Accordingly, since the vibration motor must generate that much more vibrations, it is considered to be ineffective.

To generate that much more vibrations, a larger vibration motor should be installed, more power should be supplied, and the size of the toothbrush should be increased, which all contribute to the ineffectiveness.

DISCLOSURE

Technical Problem

The present disclosure is designed to solve the problems of the prior art, and therefore it is an object of the present disclosure to provide an electric toothbrush, which may transfer vibrations to bristles efficiently without enhancing the power of a vibration motor, reduce its size, and reduce the thickness of a head portion by installing the vibration motor at the head portion.

Technical Solution

In one aspect, the present disclosure provides an electric toothbrush including a head portion and a grip, wherein the electric toothbrush further includes bristles held at the upper surface of the head portion; and a vibration motor installed in the head portion.

The vibration motor may be installed in the motor housing.

The head portion may include a bristle holder which holds the bristles; and a head plate installed to a lower side of the bristle holder so that the vibration motor is located thereat, wherein the bristle holder is installed to be integrated with the head plate or selectively separated from the head plate.

The electric toothbrush may further include a power source member provided at an inner or outer portion of the grip to operate the vibration motor.

The vibration motor may have a hexahedral shape with a length of 2 mm to 20 mm, a width of 2 mm to 30 mm and a thickness of 0.1 mm to 30 mm, or a cylindrical shape with a diameter of 1 mm to 20 mm and a thickness of 0.1 mm to 30 mm.

The head portion may include a bristle holder to which the bristles are thermally bonded and fixed; and a head plate installed to a lower side of the bristle holder, wherein the bristle holder has holes formed therein into which the bristles are inserted, and wherein the bristle holder and the head plate are coupled to form an inner space therebetween in which the vibration motor is installed.

The bristles may be held to a bristle holder which is coupled to a head plate, and a fixing groove may be formed in the upper surface of the head plate to fix the vibration motor.

The fixing groove may be formed at a center of the upper surface of the head plate.

In the case the vibration motor is installed in the fixing groove and the bristle holder is coupled to the head plate, the upper surface of the vibration motor may come into contact with the lower surface of the bristle holder.

A first insert portion may be formed at the rear end of the head portion, a second insert portion may be formed at the grip, and an insert member may be installed into the first and second insert portions, and a battery for operating the vibration motor and a switch for supplying or intercepting power of the battery to the vibration motor may be installed at the insert member.

A communication hole may be formed in the head portion to make the first insert portion communicate with the outside, and the switch may expose out through the communication hole.

A screw thread may be formed at the rear end of the head portion and a screw thread engaged with the screw thread of the head portion may be formed at the front end of the grip so that the head portion and the grip are screw-coupled.

A connection passage for communicating the first insert portion and the fixing groove may be formed in the head portion, and a cable for supplying power of the battery to the vibration motor may be installed at the connection passage.

DESCRIPTION OF DRAWINGS

Other objects and aspects of the present disclosure will become apparent from the following descriptions of the embodiments with reference to the accompanying drawings in which.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the spirit and scope of the disclosure.

Figure 1:
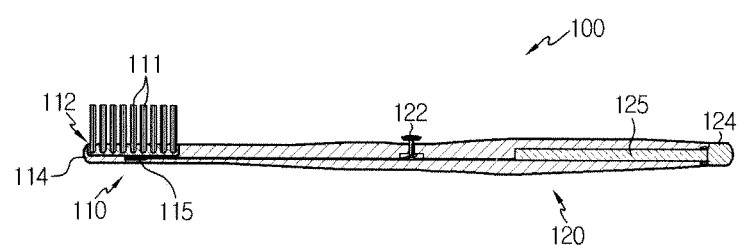
FIG. 1 is a cross-sectional view showing an electric toothbrush according to a preferred embodiment of the present disclosure.
Figure 2:
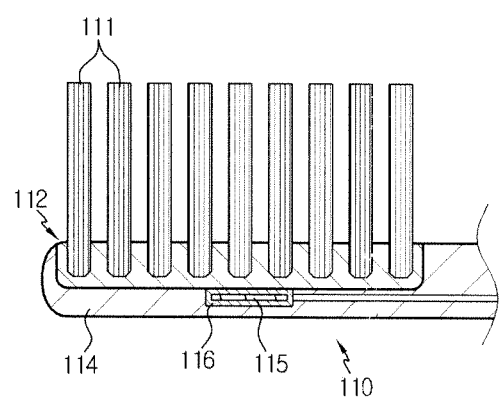
FIG. 2 is a partial cross-sectional view showing a head portion employed in the electric toothbrush according to a preferred embodiment of the present disclosure.
Figure 3:
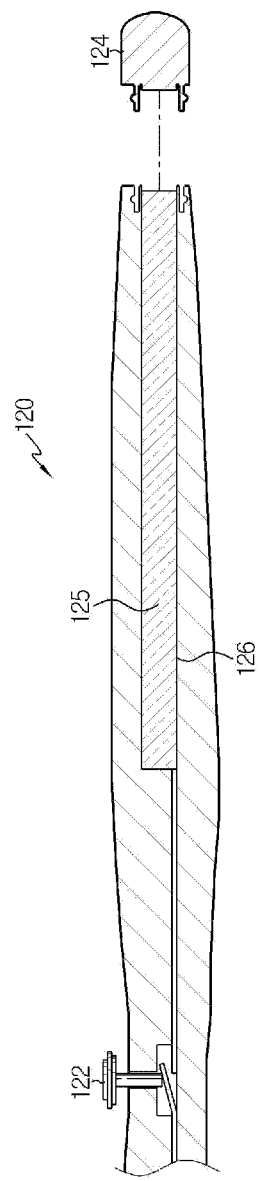
FIG. 3 is a cross-sectional view showing a grip employed in the electric toothbrush according to a preferred embodiment of the present disclosure.

FIG. 1 is a cross-sectional view showing an electric toothbrush according to a preferred embodiment of the present disclosure, FIG. 2 is a partial cross-sectional view showing a head portion employed in the electric toothbrush according to a preferred embodiment of the present disclosure, and FIG. 3 is a cross-sectional view showing a grip employed in the electric toothbrush according to a preferred embodiment of the present disclosure.

Referring to FIGS. 1 to 3, the electric toothbrush 100 includes a head portion 110 provided with a vibration motor 115, a grip 120 coupled to the head portion 110, and, a power source member for operating the vibration motor 115.

The head portion 110 includes a bristle holder 112 holding bristles 111, and a head plate 114 at which the vibration motor 115 is installed.

The bristles 111 are made of any one material selected from the group consisting of nylon-based and polyester-based materials, and the bristle holder 112 holds the bristles 111 by means of anchor tufting or anchor-free tufting. In addition, the bristles 111 may be held by means of stapling using an anchor such as a wire. These methods are generally used for holding the bristles 111 to the bristle holder 112 and are not described in detail here.

The bristle holder 112 holding the bristles 111 is installed at the head plate 114. At this time, the bristle holder 112 is integrated with the head plate 114 or selectively separated from the head plate 114.

According to the present disclosure, the bristle holder 112 is preferably configured to be separated from the head plate 114. This is so that when the bristles 111 are no longer useable, just the bristle holder 112 holding the bristles 111 may be exchanged rather than the entire electric toothbrush, making it economical. In addition, if the bristle holder 112 is not separated from the head plate 114, since a strong pressure is applied during a bristle inserting process, an impact is applied to the vibration motor 115, which may increase the defect rate. Accordingly, it is preferred that the bristle holder 112 is detachably coupled to the head plate 114.

The bristle holder 112 may be detachably installed to the head plate 114 by fitting or by using various coupling structures, for example a structure using an elastic protrusion (not shown) and a groove (not shown).

The head plate 114 is made by injection molding with the vibration motor 115 being installed therein. At this time, the vibration motor 115 is subminiature and provided at the inside of the head plate 114. For example, the vibration motor 115 is subminiature with a circular or rectangular shape. In more detail, the vibration motor 115 with a hexahedral shape has a length of 2 mm to 20 mm, a width of 2 mm to 30 mm and a thickness of 0.1 mm to 30 mm, and the vibration motor 115 with a cylindrical shape has a diameter of 1 mm to 20 mm and a thickness of 0.1 mm to 30 mm. At this time, even though the vibration motor 115 has been illustrated as having a hexahedral or cylindrical shape, the vibration motor 115 may have any shape or structure as long as it may be installed in the head plate 114, without being limited thereto.

Meanwhile, in relation to the numerical range of the length of the vibration motor 115, if the length exceeds the upper limit, it is not easy to install the head plate 114, and if the length is less than the lower limit, the vibration motor 115 may be too small to efficiently transfer the vibration force to the bristle 111.

The vibration motor 115 should be installed at the lower side of the bristle holder 112. This allows the vibration force to efficiently transfer to the bristle holder 112. In other words, as the vibration motor 115 is mounted to the head plate 114, the vibration force may be directly transferred to the bristles 111 of the bristle holder 112, which may enhance the cleaning power.

Meanwhile, in order to transfer the vibration force to the bristle holder 112 more efficiently, the vibration motor 115 may be installed to contact the lower surface of the bristle holder 112. At this time, in order to prevent the vibration motor 115 from contacting water, namely for waterproofing, the vibration motor 115 is received in the motor housing 116 and installed to the head plate 114. In other words, as shown in FIG. 2, the vibration motor 115 is received in the motor housing 116 in a sealed state, and the vibration motor 115 receives power from a power source member.

Additionally, the bristle holder 112, the head plate 114 and the grip 120, described later, may be made of plastic material by means of injection molding. At this time, the plastic material may be polypropylene (PP), polyethylene (PE), acrylonitrile-butadiene-styrene copolymer (ABS) or the like.

Meanwhile, the power source member is provided at the inner or outer portion of the electric toothbrush 100. For example, the power source member is preferably provided at the grip 120 of the electric toothbrush 100. The power source member includes a battery 125 for supplying power to the vibration motor 115 and a switch 122 for supplying the power of the battery 125 to the vibration motor 115 or intercepting the supplied power.

In other words, the power source member may be installed at the inner or outer portion of the grip 120. Hereinafter, the case where the power source member is installed at the inner portion of the grip 120 will be described.

As described above, the grip 120 is configured to receive the battery 125 therein. In other words, a battery mounting portion 126 for receiving the battery 125 is formed in the grip 120. The battery mounting portion 126 may be integrated with the grip 120 but is preferably configured to allow exchange of the battery 125.

For example, a cover 124 is installed at the end of the grip 120, namely at a side opposite to the head portion 110, and the battery 125 may be exchanged after separating the cover 124. Additionally, the body of the grip 120 may be partially separated from the grip 120 in order to allow the battery 125 to be exchanged.

Meanwhile, the switch 122 for supplying the power of the battery 125 to the vibration motor 115 or intercepting the supplied power is provided at the grip 120. The switch 122 is preferably formed at a portion where the finger of the user is located when the user grips the grip 120, for convenient manipulation.

Even though the switch 122 is illustrated and described as having a one-button structure for supplying or intercepting power by a pressing motion, the present disclosure is not limited thereto, and the switch 122 may have a two-button structure in which one button is used for supplying power and the other button is used for intercepting power.

The structure for supplying or intercepting power by using the above switch 122 is already well known in the art and thus not described in detail here. Additionally, the switch 122 may also be configured to adjust the power transferred to the vibration motor 115 according to the number of pressing manipulations.

Meanwhile, the power source member may also be installed at the outer portion of the electric toothbrush 100. In other words, the electric toothbrush 100 may be operated with the power supplied from the outside. For example, a mounting portion (not shown) where the power source member is installed may be separately provided at the outer portion of the electric toothbrush 100 so that the power source member is selectively coupled to the mounting portion. At this time, the battery 125 of the power source member installed at the mounting portion may be electrically connected to or disconnected from the vibration motor 115 by means of the switch 122.

Even though it has been illustrated and described that the electric toothbrush 100 configured as above is classified into the head portion 110 and the grip 120 so that the head portion 110 and the grip 120 are connected to each other, the head portion 110 and the grip 120 may be integrally formed but made by injection-molding upper and lower plates and then coupling the plates. In addition, it is also possible that the vibration motor 115, the switch 122 and the battery 125 are mounted thereto.

Figure 4:
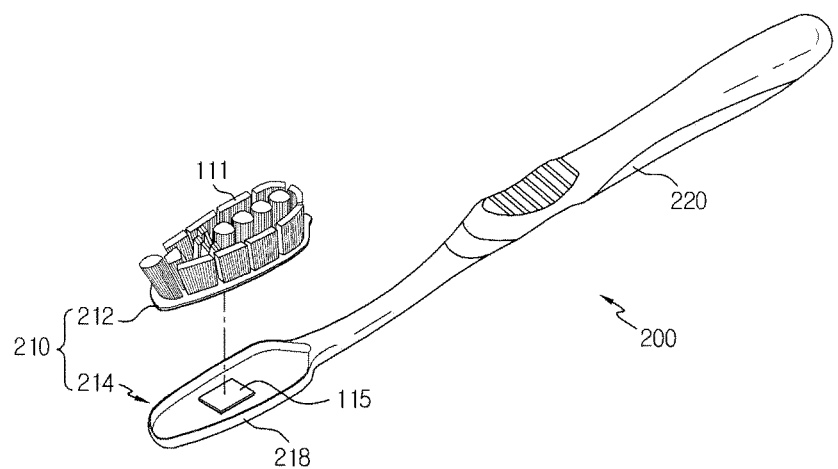
FIG. 4 is an exploded perspective view showing an electric toothbrush according to another preferred embodiment of the present disclosure.

Meanwhile, FIG. 4 is an exploded perspective view showing an electric toothbrush according to another preferred embodiment of the present disclosure.

Referring to FIG. 4, the electric toothbrush 200 includes a head portion 210 provided with the vibration motor 115, a grip 220 coupled to the head portion 210, and a power source member for operating the vibration motor 115. The grip 220 and the power source member are substantially identical to the grip 120 and the power source member of the former embodiment and thus not described in detail here.

The head portion 210 includes a bristle holder 212 holding the bristles 111 and a head plate 214 coupled to the bristle holder 212. The vibration motor 115 is installed at the head plate 214. Even though a cable connecting the vibration motor 115 and the battery is not shown in the figure, the configuration of connecting the vibration motor 115 and the battery by using a cable is obvious to those skilled in the art.

Figure 5:
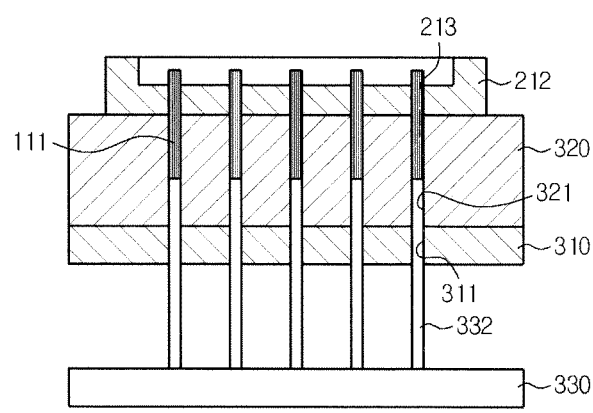
FIGS. 5 and 6 are cross-sectional views for illustrating a process of thermally bonding bristles to a bristle holder of the electric toothbrush of FIG. 4.

The bristle holder 212 includes a plurality of holes 213 and a protrusion formed at a rim portion thereof, as shown in FIG. 5.

The bristles are inserted into the holes 213 and thermally bonded therein. The protrusion is formed at the rim on the lower surface of the bristle holder 212 and is coupled to the rim protrusion 218.

In the case the bristle holder 212 is installed at the head plate 214, a space is formed between the head plate 214 and the bristle holder 212, and the space may be used to install the vibration motor 115.

Figure 6:
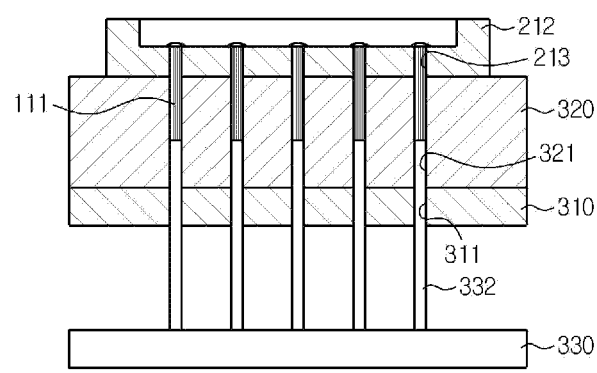

FIGS. 5 and 6 illustrate a process of thermally bonding the bristles to the bristle holder 212.

First, a first receiver 310, a second receiver 320 and a bristle holder 212 are stacked in order, and a push plate 330 is installed below the first receiver 310. At this time, the communication hole 311 of the first receiver 310, the communication hole 321 of the second receiver 320 and the holes 213 of the bristle holder 212 communicate with each other.

Subsequently, the bristles 111 are inserted into the communication holes 311, and then the push plate 330 is lifted up so that insert rods 332 are inserted into the communication holes 311, 321. If the insert rods 332 move upward in a state of being inserted into the communication holes 311, 321, the bristles 111 also move upward.

If the bristles 111 protrude upward through the holes 213 by means of the insert rods 332, the protruding portions of the bristles 111 are thermally bonded and fixed.

As described above, the bristle holder 212 of this embodiment is coupled to the head plate 214 after the bristles 111 are fixed to the holes 213 by thermal bonding in advance. Therefore, even if the bristle holder 212 may not have a thickness enough for anchor tufting, the thickness of the head may be reduced.

Figure 7:
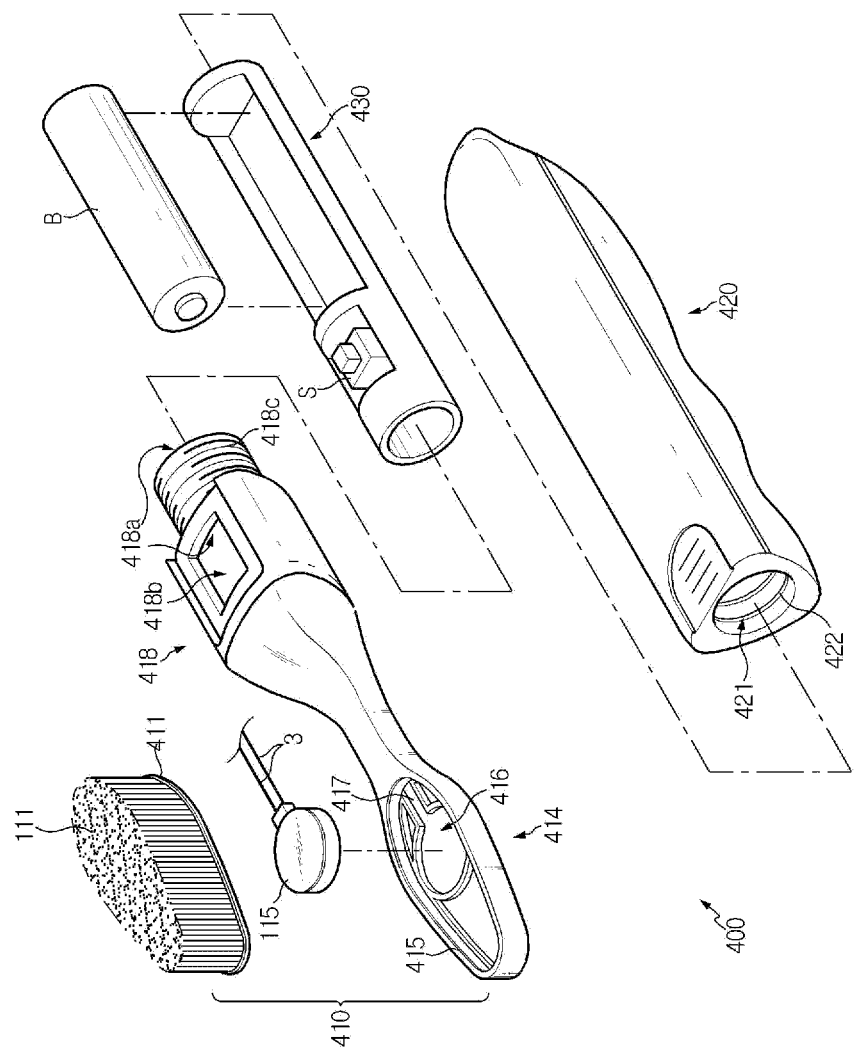
FIG. 7 is an exploded perspective view showing an electric toothbrush according to another preferred embodiment of the present disclosure.
Figure 8:
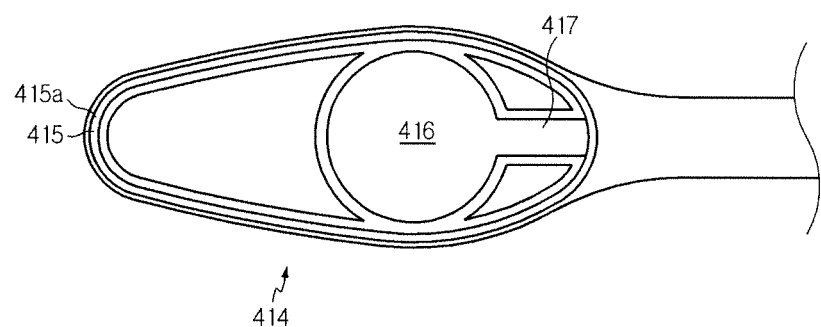
FIG. 8 is a plane view showing a head plate employed in the electric toothbrush of FIG. 7.
Figure 9:
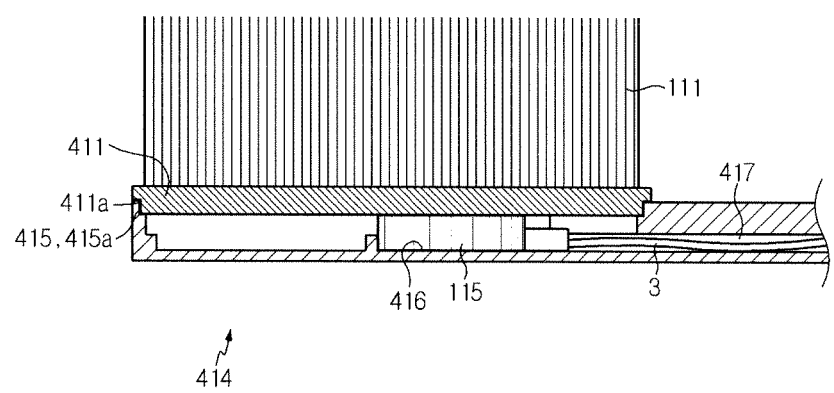
FIG. 9 is a cross-sectional view showing a head plate and a bristle holder employed in the electric toothbrush of FIG. 7.

Meanwhile, FIG. 7 is an exploded perspective view showing an electric toothbrush according to another preferred embodiment of the present disclosure, FIG. 8 is a plane view showing a head plate employed in the electric toothbrush of FIG. 7, and FIG. 9 is a cross-sectional view showing a head plate and a bristle holder employed in the electric toothbrush of FIG. 7.

Referring to FIGS. 7 to 9, the electric toothbrush 400 includes a head portion 410 where the vibration motor 115 is installed, a grip 420, and an insert member 430 inserted into the head portion 410 and the grip 420.

The head portion 410 includes a bristle holder 411, a head plate 414, and a connection portion 418 extending from the head plate 414.

The bristles 111 are installed at the bristle holder 411. The material and holding manner of the bristles 111 are substantially identical to those of the former embodiments and thus not described in detail here.

Among the holding methods described above, the anchor-free tufting is preferred, in which the bristle holder 411 may serve as an insert plate. In this case, since the bristles 111 are fixed to the bristle holder 411 by thermal bonding in advance, even if the bristle holder may not have a thickness enough for anchor tufting, the thickness of the head portion 410 may be reduced. In particular, the anchor-free tufting is preferred in view of the space prepared in the head portion 410 for the insertion of the vibration motor 115.

The bristle holder 411 holding the bristles 111 may be integrally coupled to the head plate 414 or installed to be detachable from the head plate 414.

The bristle holder 411 may be integrally coupled to the head plate 414 by ultrasonic welding of the bristle holder 411 to a rim 415 of the head plate 414. The ultrasonic welding prevents water from penetrating between the bristle holder 411 and the head plate 414, and accordingly the inner space where the vibration motor 115 is installed may be waterproof.

The bristle holder 411 may be detachably installed to the head plate 414 by fitting or by using various coupling structures, for example a structure using an elastic protrusion (not shown) and a groove (not shown). If the bristle holder 411 is detachably installed to the head plate 414, when the bristles 111 are no longer useable, the electric toothbrush is economical in that just the bristle holder 411 may be exchanged instead of exchanging the entire toothbrush. In addition, if the bristle holder 411 is not separated from the head plate 114, since a strong pressure is applied during a bristle inserting process, an impact is applied to the vibration motor 115, which may increase the defect rate.

The head plate 414 includes a fixing groove 416 formed at the upper surface thereof, and a connection passage 417 connected to the fixing groove 416. The fixing groove 416 is sized and shaped to receive and fix the vibration motor 115, and preferably sized and shaped to engage with the vibration motor 115. The fixing groove 416 fixes the vibration motor 115 to prevent the vibration motor 115 from arbitrarily moving due to vibrations and reducing noise caused by shaking of the vibration motor 115.

In addition, the electric toothbrush 400 of this embodiment may have a reduced thickness of the head portion 410 in comparison to an existing electric toothbrush without the fixing groove 416, since the vibration motor 115 is installed in the fixing groove 416.

Moreover, the fixing groove 416 is preferably formed at the center of the upper surface of the head plate 414. If the vibration motor 115 is installed at the center of the upper surface of the head plate 414, it is possible to generate vibrations more efficiently, thereby designing the vibration motor 115 to be smaller in size, and reducing the battery energy, in comparison to the case where the vibration motor 115 is installed at an edge of the head plate 414.

Further, the fixing groove 416 has a predetermined depth. In the case the bristle holder 411 is installed at the head plate 414 and the vibration motor 115 is installed in the fixing groove 416, the depth of the fixing groove 416 may be preferably set to allow the upper surface of the vibration motor 115 to come into contact with the lower surface of the bristle holder 411. If the upper surface of the vibration motor 115 comes into contact with the lower surface of the bristle holder 411, the vibrations of the vibration motor 115 may be directly transferred to the bristle holder 411.

Meanwhile, the vibration motor 115 has a common structure in that it transforms electric energy into vibrations. The vibration motor 115 may be a cylinder type or a flat type; although more preferably a flat type in order to be installed in the fixing groove 416, without being limited thereto.

The connection passage 417 is formed to connect to the fixing groove 416 and a first insert portion 418a. A cable 3 for supplying power to the vibration motor 115 is installed at the connection passage 417.

Meanwhile, a stepped projection 415a is formed at the rim 415 of the head plate 414 of this embodiment. The stepped projection 415a engages with a projection 411a formed on the lower surface of the bristle holder 411. Therefore, the bristle holder 411 is located at the head plate 414 so that the projection 411a is placed on the stepped projection 415a, and then the bristle holder 411 and the head plate 414 are coupled by means of ultrasonic welding or the like.

The connection portion 418 is formed to extend from the head plate 414. A first insert portion 418a communicating with the connection passage 417 is formed in the connection portion 418, and a screw thread 418c is formed at the outer circumference of the connection portion 418.

The connection passage 417 is formed along the length direction of the connection portion 418 to communicate with the first insert portion 418a. The cable 3 is installed at the connection passage 417 and the first insert portion 418a.

The first insert portion 418a is formed at the rear end of the head portion 410. A front end of the insert member 430 is partially inserted into the first insert portion 418a. Therefore, the cable for supplying power to the vibration motor 115 is connected to the vibration motor 115 while passing through the insert member 430, the first insert portion 418a and the connection passage 417 in order.

Preferably, the first insert portion 418a has a length which allows a switch S of the insert member 430 to be located corresponding to the communication hole 418b in a state where the head portion 410 and the grip 420 are coupled.

The screw thread 418c is screwed with a screw thread 422 of the grip 420, and accordingly the head portion 410 and the grip 420 may be coupled. The electric toothbrush 400 of this embodiment may prevent the head portion 410 from arbitrarily rotating in operation since the head portion 410 and the grip 420 are screwed.

In addition, when battery B of the toothbrush 400 of this embodiment needs to be exchanged, it is convenient in that it may be instantly exchanged by releasing the screwed coupling, unlike the conventional electric toothbrush in which the grip had to be dissembled or the battery had to be drawn from the grip in order to exchange the battery B.

The grip 420 is gripped by the hand of a user brushing his teeth. The grip 420 may be made of the same material as the grip 420 of the former embodiment. The grip 420 includes a second insert portion 421 extending from its front end along the length direction thereof with a predetermined length.

A rear end of the insert member 430 is partially inserted into the second insert portion 421. Preferably, the second insert portion 421 has a length which allows the switch S of the insert member 430 to be located corresponding to the communication hole 418b in a state where the head portion 410 and the grip 420 are coupled.

The screw thread 422 may be formed at the entrance of the second insert portion 421. The screw thread 422 may be screwed with the screw thread 418c of the connection portion 418. By the screwed coupling, the head portion 410 and the grip 420 are coupled to each other, and also it is possible to prevent the head portion 410 from arbitrarily rotating in operation.

The insert member 430 is installed into and installed in the first and second insert portions 418a, 421. In other words, the front end of the insert member 430 is inserted into the first insert portion 418a, and the rear end of the insert member 430 is inserted into the second insert portion 421.

A switch fixing portion and a battery fixing portion are provided at the insert member 430.

The switch S is installed at the switch fixing portion. The switch S supplies power of the battery B to the vibration motor 115 or intercepts the supplied power. After the insert member 430 is inserted into and installed in the first and second insert portions 418a, 421, if the grip 410 and the head portion 420 are coupled to each other, the switch S is located at a place corresponding to the communication hole 418b and thus exposes out. Accordingly, the user may operate the electric toothbrush 400 by pressing the switch S.

The battery fixing portion is provided at the rear of the switch fixing portion and may fix the battery B of a predetermined size. Positive and negative terminals of the battery B may be fixed to the battery fixing portion by using a common structure and is not described in detail here.

The present disclosure has been described in detail. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

Industrial Applicability

The electric toothbrush according to the present disclosure gives the following effects.

First, since the vibration motor is installed in the head portion, the vibration force may be directly transferred to the bristle holder, which enhances the cleaning power. Therefore, plaque on the tooth surface may be effectively removed. In particular, since the vibration motor comes into contact with the bristle holder, the vibrations of the vibration motor may be effectively transferred to the bristle holder.

Second, since the vibration motor may be operated by a small power, the energy consumption of the battery may be reduced.

Third, since a subminiature vibration motor is installed at the head portion, the size of the toothbrush may be reduced.

Fourth, the vibration motor may be stably fixed in the head portion. Accordingly, the vibration motor may be fixed at a location where the bristle holder may be vibrated in the most efficient way.

Fifth, the grip and the head portion may be coupled in a stable way, and it is possible to prevent the head portion from rotating when a user cleans his teeth.

Sixth, since the vibration motor is fixed in the fixing groove, it is possible to reduce noise caused by shaking of the vibration motor.

Seventh, since the vibration motor is fixed in the fixing groove, the thickness of the head portion may be reduced.

What is claimed is:

1. An electric toothbrush comprising:
   a head portion including:
      a bristle holder having a plurality of holes;
      bristles respectively inserted into the holes so that lower ends of the bristles protrude below the bristle holder, the lower ends of the bristles being thermally bonded to a lower surface of the bristle holder;
      a head plate installed to a lower side of the bristle holder;
      a fixing groove formed in an upper surface of the head plate; and
      a vibration motor installed in the fixing groove in a manner that a lower portion of the vibration motor is fit into the fixing groove; and
   a grip coupled to the head portion,
   wherein the fixing groove has a shape corresponding to the lower portion of the vibration motor so that the lower portion of the vibration motor is fit therein, and
   wherein, in the case the bristle holder is coupled to the head plate, an upper surface of the vibration motor comes into contact with a lower surface of the bristle holder.

2. The electric toothbrush according to claim 1, wherein the bristle holder is installed to be integrated with the head plate or selectively separated from the head plate.

3. The electric toothbrush according to claim 1, further comprising a power source member provided at an inner or outer portion of the grip to operate the vibration motor.

4. The electric toothbrush according to claim 1, wherein the vibration motor has a hexahedral shape with a length of 2 mm to 20 mm, a width of 2 mm to 30 mm and a thickness of 0.1mm to 30 mm, or a cylindrical shape with a diameter of 1 mm to 20 mm and a thickness of 0.1 mm to 30 mm.

5. The electric toothbrush according to claim 1, wherein the bristle holder and the head plate are coupled to form an inner space therebetween in which the vibration motor is installed.

6. The electric toothbrush according to claim 1, wherein the fixing groove is formed at a center of the upper surface of the head plate.

7. The electric toothbrush according to claim 1, wherein a first insert portion is formed at the rear end of the head portion, a second insert portion is formed at the grip, and an insert member is installed into the first and second insert portions, and
   wherein a battery for operating the vibration motor and a switch for supplying or intercepting power of the battery to the vibration motor are installed at the insert member.

8. The electric toothbrush according to claim 7, wherein a communication hole is formed in the head portion to make the first insert portion communicate with the outside, and the switch exposes out through the communication hole.

9. The electric toothbrush according to claim 7, wherein a screw thread is formed at the rear end of the head portion and a screw thread engaged with the screw thread of the head portion is formed at the front end of the grip so that the head portion and the grip are screw-coupled.

10. The electric toothbrush according to claim 7,
   wherein a connection passage for communicating the first insert portion and the fixing groove is formed in the head portion, and
   wherein a cable for supplying power of the battery to the vibration motor is installed at the connection passage.

* * * * *